US010088423B2

United States Patent
Lin et al.

(10) Patent No.: US 10,088,423 B2
(45) Date of Patent: Oct. 2, 2018

(54) DISPOSABLE SETS INCLUDING RAMAN SENSORS

(71) Applicants: Baxter International Inc., Deerfield, IL (US); Baxter Healthcare SA, Glattpark (Opfikon) (CH)

(72) Inventors: Rongsheng Lin, Buffalo Grove, IL (US); James Slepicka, Genoa City, IL (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 54 days.

(21) Appl. No.: 15/036,004

(22) PCT Filed: Sep. 8, 2014

(86) PCT No.: PCT/US2014/054508
§ 371 (c)(1),
(2) Date: May 11, 2016

(87) PCT Pub. No.: WO2015/035285
PCT Pub. Date: Mar. 12, 2015

(65) Prior Publication Data
US 2017/0199128 A1    Jul. 13, 2017

Related U.S. Application Data

(60) Provisional application No. 61/875,447, filed on Sep. 9, 2013.

(51) Int. Cl.
*G01J 3/44*    (2006.01)
*G01N 21/65*    (2006.01)

(52) U.S. Cl.
CPC .......... *G01N 21/658* (2013.01); *G01N 21/65* (2013.01); *G01N 2021/651* (2013.01)

(58) Field of Classification Search
CPC ...... G01N 21/65; G01N 21/658; G01N 21/05; G01N 2021/651; G01J 3/44; C12Q 2565/632
(Continued)

(56) References Cited

U.S. PATENT DOCUMENTS 6,623,977 B1    9/2003    Farquharson et al.
7,713,849 B2    5/2010    Habib et al.
(Continued)

FOREIGN PATENT DOCUMENTS

CN    102 279 175    12/2011

OTHER PUBLICATIONS

Written Opinion of the International Searching Authority—PCT/US2014/054508 dated Jan. 21, 2015—10 pages.
(Continued)

*Primary Examiner* — Tarifur Chowdhury
*Assistant Examiner* — Jonathon Cook
(74) *Attorney, Agent, or Firm* — K&L Gates LLP (57) ABSTRACT

A disposable set (100) includes a tube; and a sensing member (104) press-fittingly insertable into the tube, the sensing member including: a first end (106) having a first diameter and including at least one through hole (112) positioned along a perimeter of the first end; a second end (108) having a second diameter and including at least one through hole positioned along a perimeter of the second end, the first diameter and the second diameter being substantially equal to an interior diameter of the tube; and a middle portion (110) located between the first end and the second end having a diameter that is less than the first diameter, the middle portion including at least one SERS sensing element (114), wherein the through holes in the first and second ends enable fluid to pass through the sensing member.

16 Claims, 8 Drawing Sheets

(58) Field of Classification Search
USPC .......................................................... 356/301
See application file for complete search history.

(56) References Cited

U.S. PATENT DOCUMENTS

| | | | |
|---|---|---|---|
| 8,670,119 B1* | 3/2014 | Bratkovski | ............ G01N 21/05 |
| | | | 356/301 |
| 2012/0242987 A1 | 9/2012 | Liu et al. | |
| 2012/0276549 A1 | 11/2012 | Cunningham et al. | |
| 2014/0036263 A1* | 2/2014 | Kim | ..................... G01N 21/658 |
| | | | 356/301 |

OTHER PUBLICATIONS

International Searching Authority—PCT/US2014/054508 dated Jan. 21, 2015—4 pages.
European Search Report—Appl. No. 17195282.3-1554—dated Dec. 15, 2017, 2 pages.
Charles J. Choi et al., "Biochemical sensor tubing for point-of-care monitoring of intravenous drugs and metabolites", Lab on a Chip, vol. 12, No. 3, Dec. 12, 2012, XP055428814, pp. 574-581.

* cited by examiner

DISPOSABLE SETS INCLUDING RAMAN SENSORS

PRIORITY CLAIM

The present application is a National Phase of International Application No. PCT/US2014/054508, filed on Sep. 8, 2014, which claims priority to U.S. Provisional Patent Application No. 61/875,447, filed Sep. 9, 2013, the entire contents of each of which are incorporated herein by reference and relied upon.

TECHNICAL FIELD

The present disclosure relates in general to surface enhanced Raman spectroscopy, and more specifically to a sensing member within a disposable set for Raman spectroscopy sensing.

BACKGROUND

Intravenous ("IV") therapy is typically provided to a patient using a disposable set. Previously, administrators had to confirm a fluid (e.g., drug) type, fluid concentration, or agent within a fluid to be administered by reading information on a drug container such as, for example, an infusion bag. However, administrators can misread the information on the container or forget to check the information on the container. Additionally, the fluid, agent and/or fluid/agent concentration within the container may not accurately reflect the actual fluid type or concentration. To reduce these errors and improve patient safety, sensors have been integrated within a portion of the disposable drug delivery set to provide a final verification before the fluid is infused into a patient.

Some of these known fluid detection sensors use optical sensing to determine a drug type and/or concentration. These optical sensors include Raman spectroscopy sensors and surface enhanced Raman spectroscopy ("SERS") sensors. The sensors use light provided from an outside source, such as a laser, to detect properties in the fluid under measurement.

Raman spectroscopy sensors measure vibrational, rotational, and other low-frequency modes of a fluid. The sensors use for example, inelastic scattering or Raman scattering of monochromatic light from a laser in the visible, near infrared, and/or near ultraviolet range. The laser light interacts with molecular vibrations, phonons, and/or other excitations in the fluid, resulting in the energy of the laser photons being shifted up or down. The shift in energy provides information about the vibrational modes in the fluid. In practice, a sample fluid is illuminated with a laser beam. Light from the illuminated spot is collected with a lens and sent through a monochromator. Wavelengths close to the laser line resulting from elastic Rayleigh scattering are filtered out while the rest of the collected light is dispersed onto a Raman spectroscopy sensor for analysis.

SERS sensors operate under the same principles as Raman spectroscopy sensors. However, SERS sensors use a surface-sensitive detection technique that enhances Raman scattering by molecules absorbed on rough metal surfaces or nanostructures such as, for example, plasmonic-magnetic silica nanotubes. Similar to Raman spectroscopy sensors, SERS sensors use laser light to detect shifts in energy of the absorbed molecules. The use of SERS sensors requires that the sensor be in contact with the fluid under measurement. Known systems position SERS sensors within the tubing of a disposable set. However, placing the SERS sensor within the tubing reduces fluid flow, thereby frustrating infusion therapy.

Moreover, the use of SERS sensors and Raman spectroscopy sensors requires that the laser light travel through the tubing. The plastic composition of the tubing oftentimes interferes with the laser light, reducing sensing accuracy of the Raman spectroscopy sensors and/or the SERS sensors. A need accordingly exists for a disposable set that uses Raman spectroscopy sensors and/or SERS sensors having improved fluid flow, and which is able to provide relatively interference-free laser light.

SUMMARY

The present disclosure provides new and innovative configurations of SERS sensors and/or Raman spectrometry sensor interfaces configured to facilitate the detection of a fluid, concentration of a fluid, and/or a concentration of an agent within a fluid through a disposable set. In some instances, the SERS sensors are located within tubing of a disposable set. In other instances, the SERS sensors and/or Raman spectrometry sensor interfaces are positioned to be flush within an interior wall of disposable set tubing. In such a configuration, the SERS sensors and/or Raman spectrometry sensor interfaces include a wing and/or an alignment key configured to accommodate and/or connect to a lens of a Raman spectrometer.

In an example embodiment, a disposable set includes a tube and a sensing member insertable into the tube. The sensing member is configured to include (i) a first end having a first diameter and at least one through hole positioned along a perimeter of the first end. The sensing member also includes a second end having a second diameter and including at least one through hole positioned along a perimeter of the second end, the second diameter being substantially equal to the first diameter. The sensing member further includes a middle portion located between the first end and the second end having a diameter that is less than the first diameter, the middle portion including at least one SERS sensing element.

In another embodiment, a disposable set includes a tube including an opening positioned along a portion of a wall of the tube and an enclosure connected to the tube at the opening. The example enclosure includes a first end including a SERS substrate positioned to be substantially flush with an interior wall of the tube at the opening and at least one post to support the SERS substrate at the opening. The example enclosure also includes a second end configured to align a sensing device with the SERS substrate and a channel located between the first end and the second end configured to enable light from the sensing device to reach the SERS substrate. In this other embodiment, the disposable set may further include a second enclosure connected to the tube at the second opening. This second enclosure includes a first end including a window positioned to be substantially flush with the interior wall of the tube at the second opening, a second end configured to align a second sensing device with the window and a channel located between the first end and the second end configured to enable light from the second sensing device reach the window.

Additional features and advantages of the disclosed SERS sensors and/or Raman spectrometry sensor interfaces are described in, and will be apparent from, the following Detailed Description and the Figures.

DETAILED DESCRIPTION

The present disclosure relates in general to a disposable set that includes a SERS sensor, and in particular, to a disposable set that is integrated with an optical Raman spectroscopy interface and/or SERS sensing element for fluid verification and/or identification during IV therapy. As disclosed herein, a SERS sensor is a sensor positioned within a disposable set. The SERS sensor includes rough metal surfaces or nanostructures configured to contact or otherwise interact with molecules of a fluid flowing through the disposable cassette. The interaction of the SERS sensor with the fluid molecules enhances Raman scattering to facilitate the detection of the fluid type, fluid concentration, and/or agent within a fluid by a SERS sensing (e.g., analysis and detection) device or Raman sensing device. The Raman spectroscopy interface includes a window or other structure that enables a Raman sensing device to detect properties of fluid (or agent) based on incident laser light.

As discussed below, the Raman spectroscopy interface and/or the SERS sensor within a disposable set is configured to facilitate the detection of laser light scattering based on fluidic (or agent) properties. The detection of the scattered laser light enables the accurate detection of a wide range of drugs without affecting a flow of fluid through the disposable set. This disclosure provides different embodiments of configurations of SERS and/or Raman sensing members having one or more sensing elements and/or interfaces integrated with a disposable set.

First Embodiment

Figure 1:
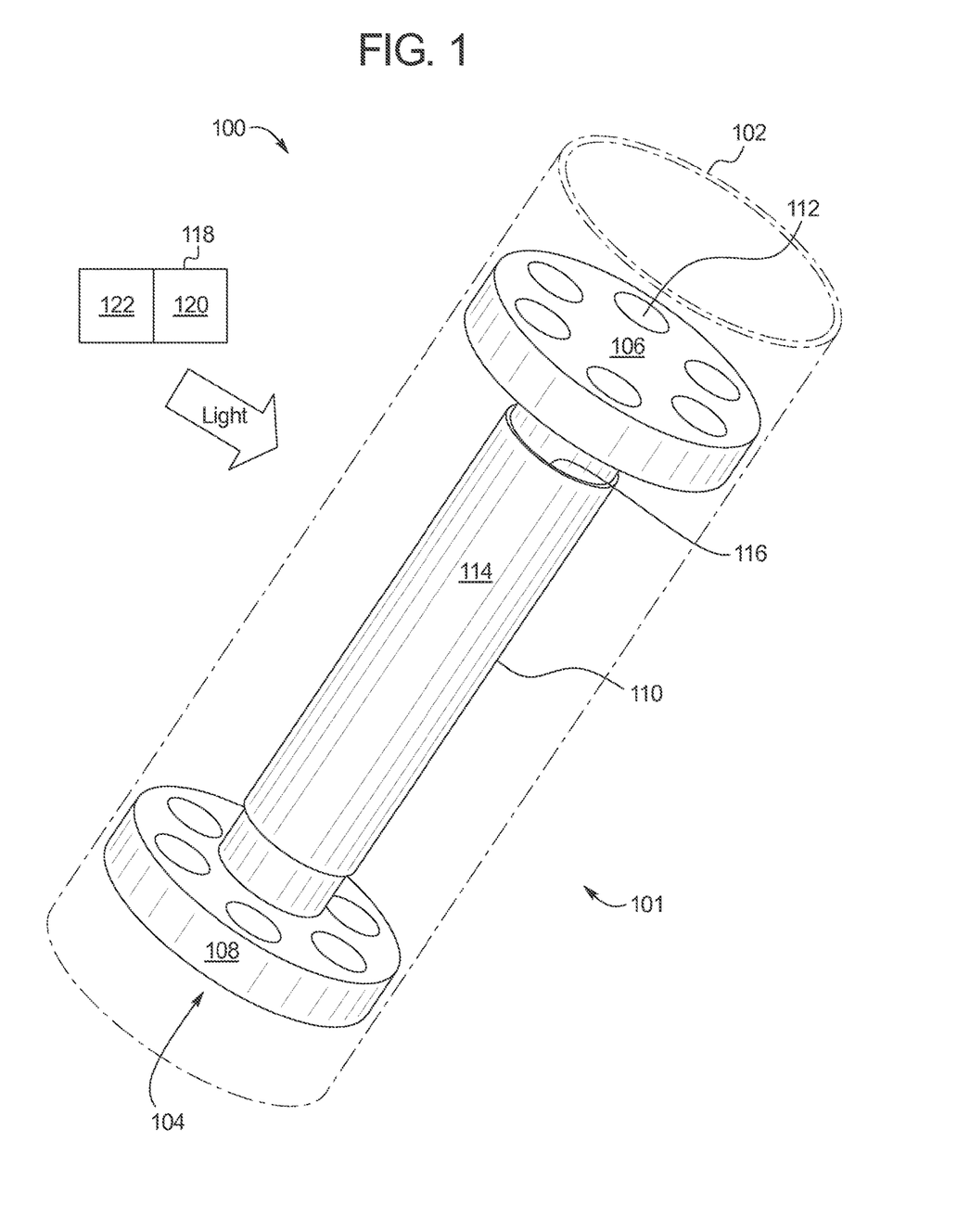
FIG. 1 shows a diagram of a disposable set including a SERS sensor disposed within a tube, according to a first embodiment of the present disclosure.

FIG. 1 shows a first embodiment of a disposable set 100 for use with a SERS sensor 101. In this illustrated embodiment, the disposable set 100 includes a tube 102 (e.g., an IV line). The tube 102 may include any type of medical fluid material including, for example, any medical grade plastic or rubber, such as silicone, polyvinylchloride (PVC), or nylon, etc. The tube 102 may have any diameter from a few millimeters to a few centimeters or larger. It should be appreciated that FIG. 1 only shows a portion of the disposable set 100 and the tube 102. For instance, the disposable set 100 can also include a catheter, a connection to an infusion bag, a connection to an infusion pump, an air removal device, etc.

In the illustrated example, the SERS sensor 101 includes a sensing member 104 disposed within the tube 102. The sensing member 104 may be inserted into the tube 102. Alternatively, the tube 102 may be formed or molded around the sensing member 104. In this example, the sensing member 104 includes a first flange 106, a second flange 108, and a middle section 110. The flanges 106 and 108 have a diameter that is substantially equal to or slightly larger (e.g., larger by 0.1 to 2 millimeters) than a diameter of an interior wall of the tube 102. Such a configuration enables the sensing member 104 to be press-fittingly inserted into the tube 102 while also holding the sensing member 104 in place during use. In other examples, the second flange 108 may have a smaller diameter than the first flange 106.

The flanges 106 and 108 include at least one through hole 112 configured to enable fluid to pass through the sensing member 104. In the illustrated example, the sensing member 104 includes six through holes 112 positioned circumferentially along a perimeter of the flanges 106 and 108. In other embodiments, the sensing member 104 may include additional or fewer through holes 112. Further, the diameters of the through holes 112 may vary based on the number of through holes 112 included within each flange 106 and 108. In some instances, the number and dimension of the through holes 112 may be based on a type of fluid (or agent) that is to pass through the tube 102. For instance, more holes and/or larger holes may be used for relatively more viscous fluids and/or more patient-critical fluids. Moreover, while the through holes 112 are shown as being circular, in other examples they may be configured to have an oval shape, a square shape, a rectangular shape, a triangular shape, etc.

The example middle section 110 of FIG. 1 is configured to have a diameter that is smaller than the flanges 106 and 108. The middle section 110 includes one or more sensing elements 114 attached to a plastic or metallic sheet 116, which may be rolled or assembled into the middle section 110 using a variety of methods including, for example, adhesive and/or heat shrinkable plastic. The sensing elements 114 include a rough metal surface or nanostructures (as described in conjunction with FIGS. 7 and 9) attached to the plastic (or metallic) sheet, which are configured to interact with molecules within the fluid to enable the acquiring of SERS measurements. In some instances, the sensing elements 114 absorb or bind to at least some molecules of a fluid under measurement. This absorption or binding enhances Raman light scattering or inelastic scattering of an incident laser light, which improves the detection of fluidic properties (e.g., vibrational, rotational, and other low-frequency modes of a fluid). The type and/or composition of the sensing elements 114 may be selected based on the fluid to be detected.

In this example, a SERS sensing device 118 includes a light emitter 120 configured to provide light (e.g., laser light) that propagates through the tube 102 to the middle section 110. The SERS sensing device 110 also includes a SERS spectrometer 122 that measures interactions of molecules within the fluid with the sensing element 114 to determine properties of the fluid. The SERS spectrometer 122 uses the detected properties to identify a fluid type and/or concentration. The SERS spectrometer 122 may include a commercial spectrometer, e.g., from Delta Nu®, Raman Systems®, and/or Control Development, for example.

Figure 5:
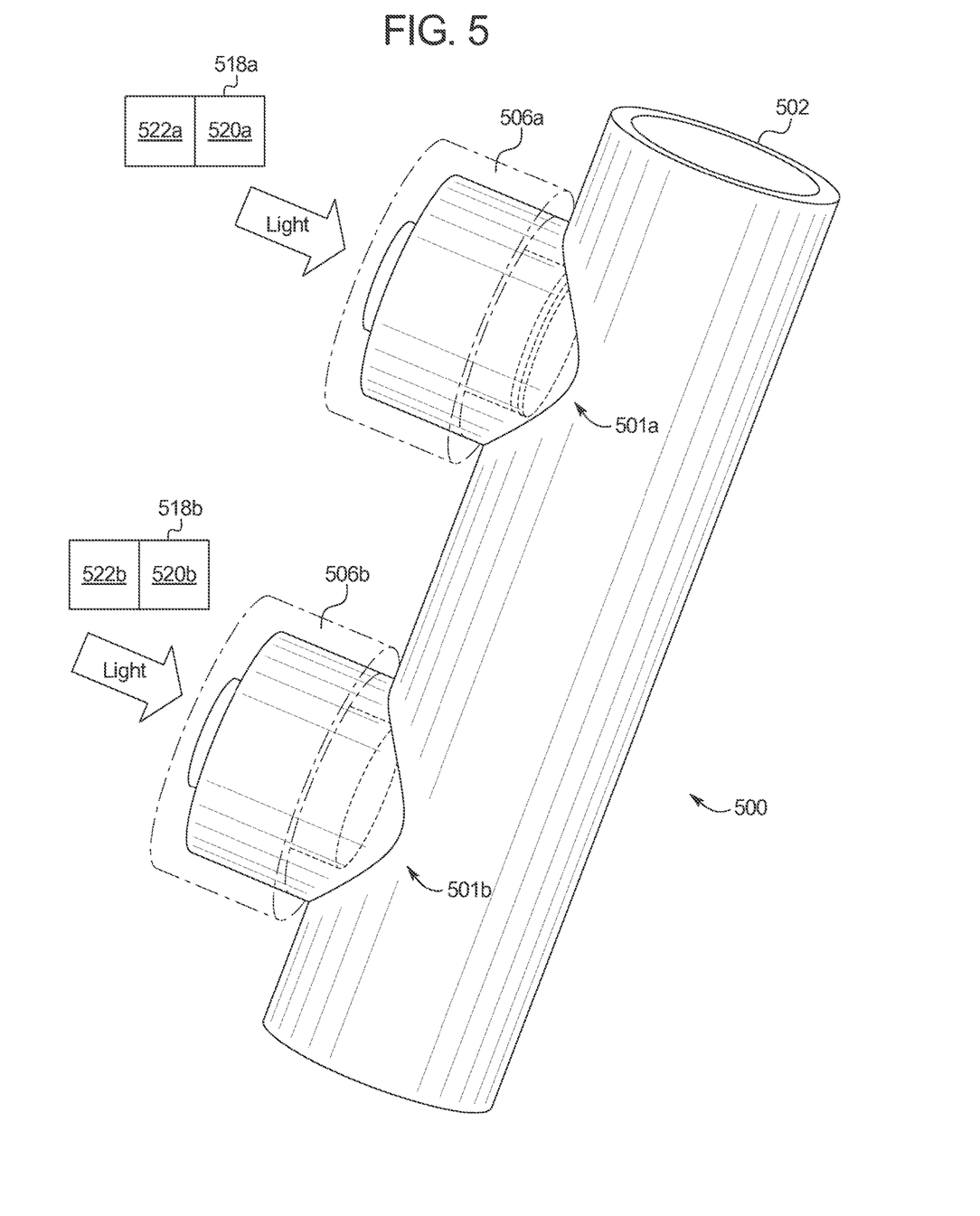
FIGS. 5 and 6 show a diagram of a disposable set including a SERS sensor and a Raman spectroscopy sensor interface integrated with a tube, according to a fourth embodiment of the present disclosure.
Figure 6:
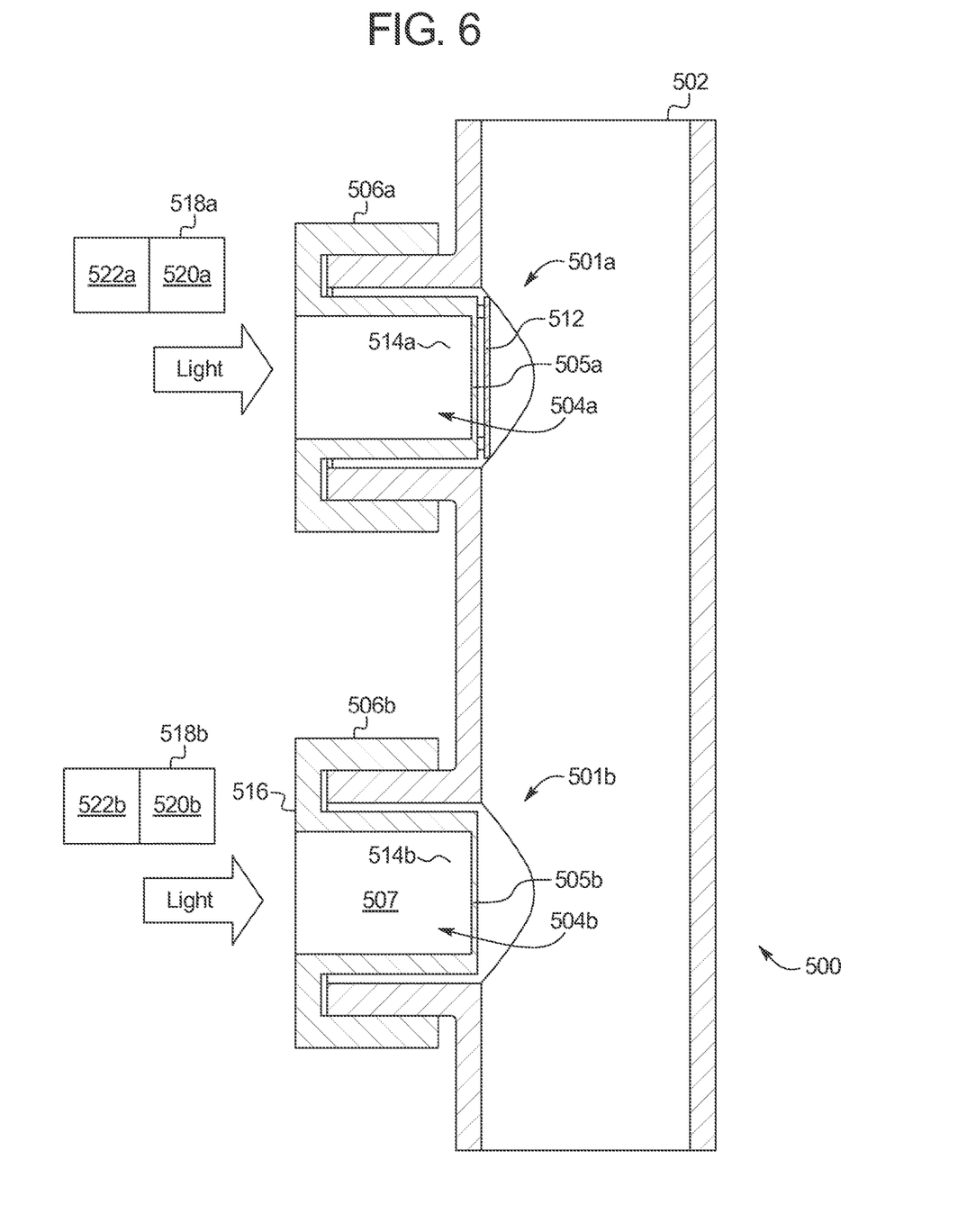

While FIG. 1 shows only the SERS-type sensing member 104, it should be appreciated that the disposable set 100 may also include a Raman spectroscopy sensor located upstream or downstream from sensing member 104, as illustrated for example in connection with FIGS. 5 and 6. As discussed above, Raman spectroscopy sensing does not require a surface to detect properties of a molecule. As a result, the Raman spectroscopy sensor may be external to the tube 102. As illustrated in FIGS. 5 and 6, the use of a Raman spectroscopy sensor in conjunction with a SERS sensor enhances fluid detection precision.

Second Embodiment

Figure 2:
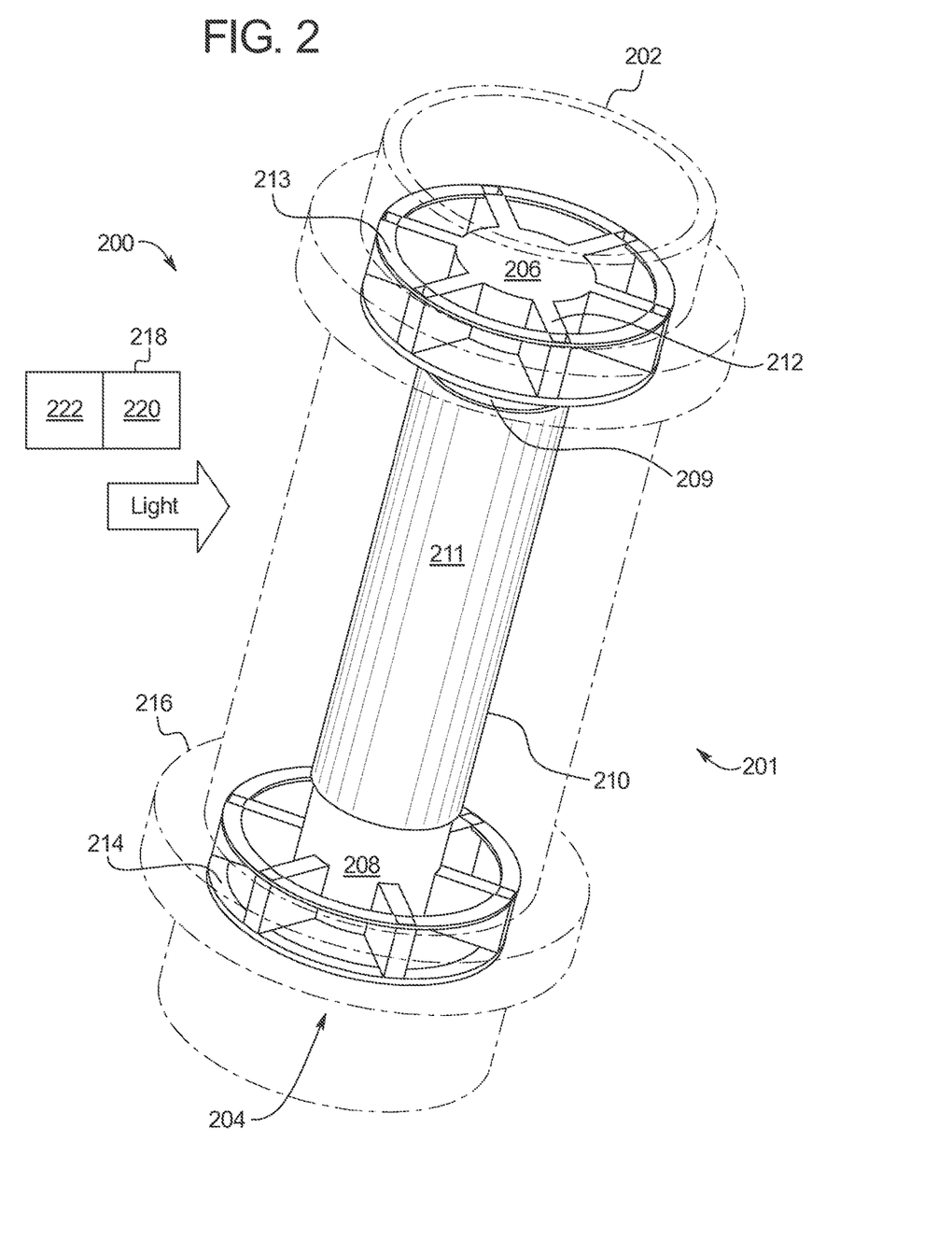
FIG. 2 shows a diagram of a disposable set including a SERS sensor disposed within a tube, according to a second embodiment of the present disclosure.

FIG. 2 shows a second embodiment of a disposable set 200 including a SERS sensor 201. In this embodiment, the disposable set 200 includes tubing 202 and sensing member 204 with first end 206, second end 208, and middle section 210. The middle section 210 includes a SERS sensing element 211. The middle section 210 also includes a step 209 that aligns the sensing element onto a center portion of the section 210.

The ends 206 and 208 include spokes or paddles 212 that extend from ends 206 and 208 to respective outer rings 213, which compress into the tube 202 for press-fitting. For instance, the spokes 212 may be compressible to enable the sensing member 204 to be inserted or press-fitted into the tube 202. Spaces defined between ends 206 and 208, spokes 212 and outer rings 213 enable fluid to pass through the sensing member 204.

To help fix the location of the sensing member 204, the example tube 202 includes interior wings 214. The interior wings 214 are configured to secure or prevent the sensing member 204 from moving after insertion. In this example, the interior wings 214 include a circular ring that extends from an interior wall of the tube 202 to contact the ends 206 and 208. In other examples, the interior wing 214 may include one or more latches that extend from the interior wall of the tubing. While FIG. 2 shows an interior wing 214 for each end 206 and 208, in other embodiments, the tube 202 may include only one interior wing 214.

The example tube 202 of FIG. 2 also includes exterior wings 216. As discussed above, a SERS sensing device 218 (including a light emitter 220 and a Raman spectrometer 222) is placed adjacent to the sensing member 204 exterior to the tube 202 to provide SERS sensing and analysis. The example exterior wings 216 extend from an exterior wall of the tube 202 to align a lens of the SERS sensing device 218 with the sensing member 204. In this embodiment, the exterior wings 216 are located in proximity to the ends 206 and 208. However, the exterior wings 216 may be located at other portions of the tube 202 based on the type of Raman spectrometer and/or lens used. Further, dimensions of the exterior wings 216 may be based on the type of Raman spectrometer and/or lens.

While the interior wings 214 and the exterior wings 216 are shown as being integrated with the tube 202, it should be appreciated that in other examples, the wings 214 and 216 may be constructed separate from the tube 202. In these examples, the wings 214 and 216 are connected to the tube 202 using adhesives, pressure bonding, heat staking, etc. Additionally, in some embodiments, the wings 214 and 216 may be adjusted by a user. For instance, a diameter of the wings 214 and 216 may be adjusted to accommodate a lens of a Raman spectrometer.

Third Embodiment

Figure 3:
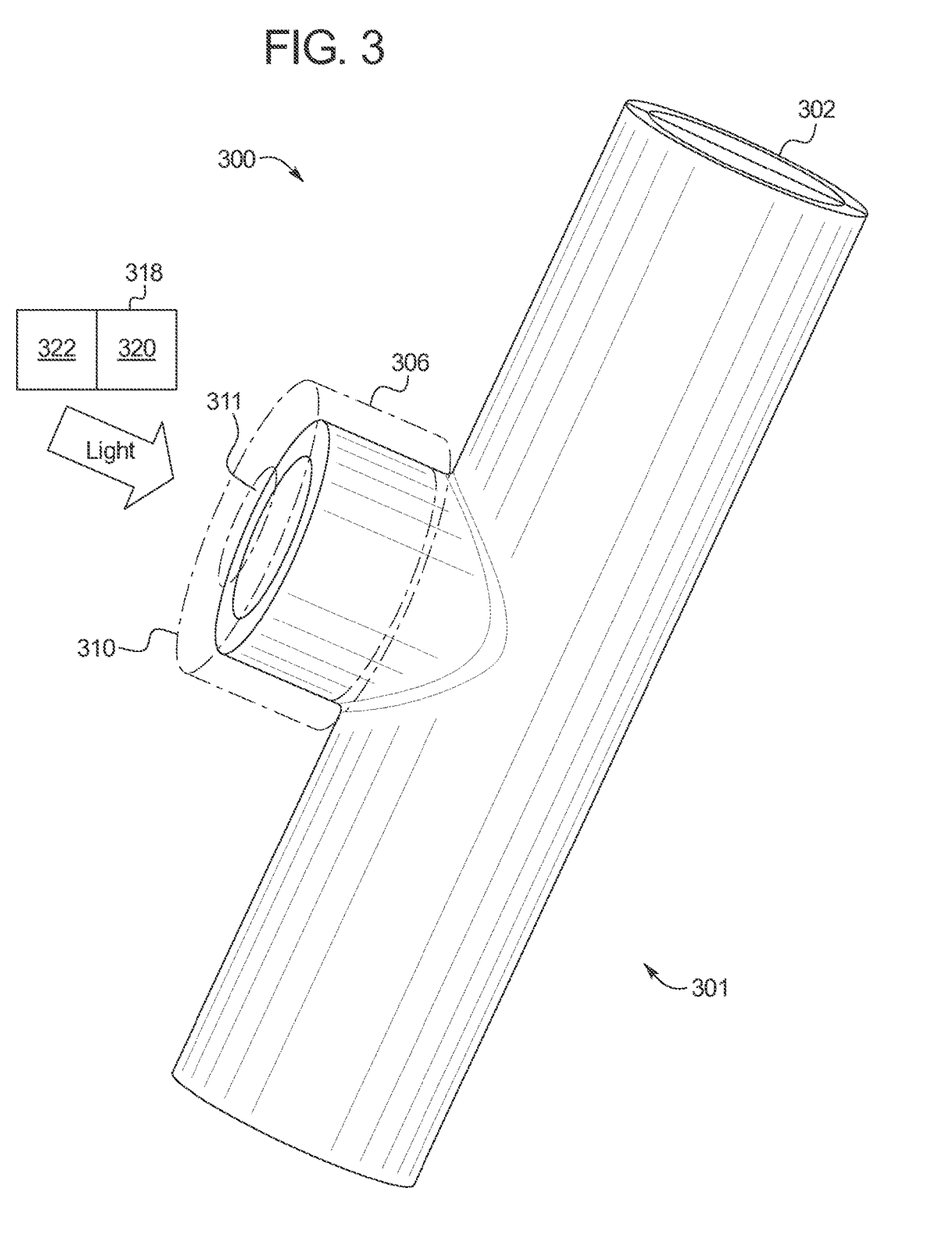
FIGS. 3 and 4 show a diagram of a disposable set including a SERS sensor integrated with a tube, according to a third embodiment of the present disclosure.
Figure 4:
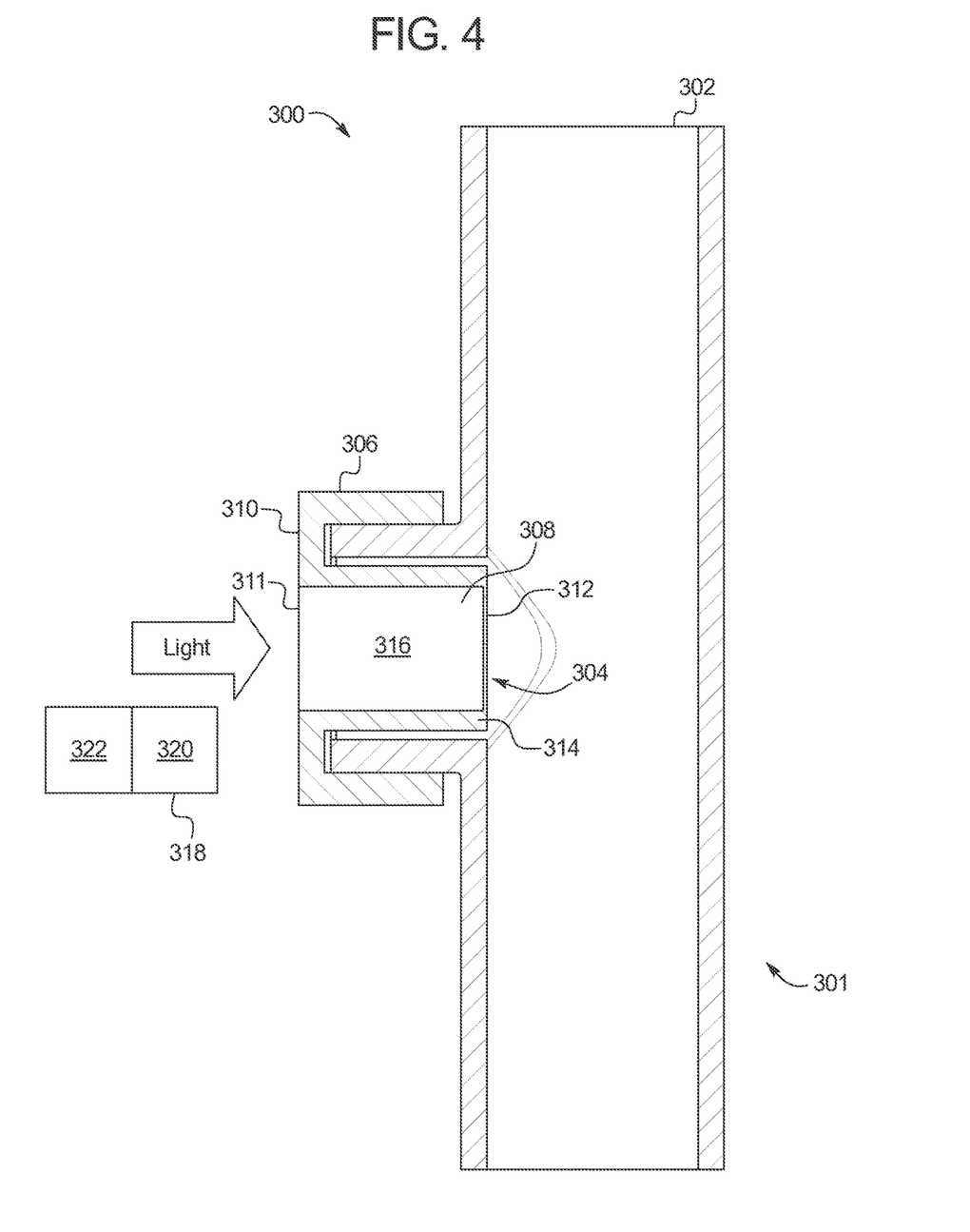

FIGS. 3 and 4 show a third embodiment of a disposable set 300 including a SERS sensor 301 integrated with a tube 302. In this embodiment, the tube 302 includes port 304 defining an opening formed in a portion of a wall of the tube 302. A cap 306 is connected to the tube 302 at the port 304. The connection of the port 304 and cap 306 may be made by induction welding and/or any other method to create a seal between the wall of the tubing 302 and the cap 306.

The example cap 306 includes a first end 308 and a second end 310. The first end 308 faces an interior of the tube 302. The second end 310 faces away from the tube and may include an alignment key 311 for a SERS sensing device 318 (including a light emitter 320 and a Raman spectrometer 322). As shown in FIG. 4, the first end 308 includes a SERS substrate 312 that is positioned to be substantially flush with the interior wall of the tube 302. The SERS substrate 312 may be supported by one or more posts 314 to prevent the substrate from moving during use. Similar to the sensing element 114 and 211 respectively of FIGS. 1 and 2, the SERS substrate 312 of FIG. 3 includes rough metal surfaces or nanostructures disposed on a plastic and/or metallic sheet (described in conjunction with FIGS. 7 and 9).

The configuration shown in FIGS. 3 and 4 enables the SERS substrate 312 to be backlight by the light emitter 320 for fluid molecule analysis while at the same time reducing the amount of area within the tube 302 used by the sensor. In comparison, the sensing members 104 and 204 of FIGS. 1 and 2 consume a relatively large volume within the tube. While through holes 112 and paddles 212 reduce fluid restriction, the volume of the members 104 and 204 still provides some fluid restriction. The configuration of FIG. 3 instead locates the SERS substrate 312 along a wall of the tube 302, thereby keeping the channel of the tube 302 relatively free of components. In some instances, the SERS substrate 312 may extend some distance (e.g., 0.1 to 10 millimeters) from the interior wall of the tube to increase the amount of contact with the fluid.

To enable light to reach the SERS substrate 312, the example cap 306 of FIG. 3 includes a channel 316 that extends from the first end 308 to the second end 310. The dimensions of the channel may vary based on the alignment key of the second end 310 and the size of the SERS substrate 312. The alignment key 311 functions as a window to enable light from the SERS sensing device 318 to travel through the channel 316 to the SERS substrate 312. In some embodiments, the channel 316 may include one or more lens to focus light on the SERS substrate 312.

Fourth Embodiment

FIGS. 5 and 6 show a fourth embodiment of a disposable set 500 including a SERS sensor 501a and a Raman spectroscopy sensor interface 501b integrated with a tube 502. In this embodiment, the SERS sensor 501a includes a SERS substrate 512a (similar to the SERS substrate 312, as discussed in conjunction with FIGS. 3 and 4). As shown in FIGS. 5 and 6, the SERS sensor 501a and the Raman spectroscopy sensor interface 501b may be directly adjacent to each other and/or separated by a few centimeters (e.g., less than 4 centimeters) along the tube 502. In other embodiments, the Raman spectroscopy sensor interface 501b may be located between 4 centimeters to at least 24 centimeters downstream and/or upstream from the SERS sensor 501a.

The Raman spectroscopy sensor interface 501b includes a window and channel to facilitate a Raman spectroscopy sensor's measurement of fluid within the tube 502. To accommodate this Raman spectroscopy sensor interface 501b, the tube 502 includes a second port 504b from which a second cap 506b is connected. The second port 504b is formed in another portion of a wall of the tube 502. Similar to the first cap 506a, the second cap 506b includes a first end 514b, a second end 516, and a channel 507. However, because Raman spectroscopy sensors do not require a sensing element that contacts the fluid, the first end 514b includes instead a window section 505b that enables light from a Raman spectrometer to propagate to the interior of the tube 502. To reduce interference, the window section 505b may be constructed from glass, quartz, or substantially transparent plastic.

In some instances, the first end 514a of the first cap 506a at the first port 504a may also include a window section 505a on the backside of the SERS substrate 512. This window section 505a may improve light transmission to the backside of the SERS substrate 512, thereby improving sensing accuracy. The SERS substrate 512 may be connected to the window section 505a via one or more posts or other connectors.

The SERS sensor 501a operates in conjunction with a SERS sensing device 518a including a light emitter 520a and a Raman spectrometer 522a. The Raman spectroscopy sensor interface 501b operates in conjunction with a Raman sensing device 518b including a light emitter 520b and a Raman spectrometer 522b. Alternatively, the SERS sensor 501a and the Raman spectroscopy sensor interface 501b operate in conjunction with a single SERS (or Raman) sensing device including a light emitter and a Raman spectrometer.

It should be appreciated that the use of a SERS sensor 501a in conjunction with a Raman spectroscopy sensor interface 501b at a similar location of the tube 502 improves fluid detection by increasing the amount of analysis performed on the fluid. For instance, the Raman spectroscopy sensor interface 501b enables information to be determined as to how laser light interacts with molecular vibrations, phonons, and/or other excitations in the fluid while the SERS sensor 501a provides information as to how laser light interacts with molecular vibrations, phonons, and/or other excitations on the SERS substrate 512. Some fluids (e.g., drugs) that may not be easily detectable by one type of sensor may be more readily detected by the other sensor. This configuration accordingly provides detection of more types of fluids.

SERS Sensing Element and Substrate Embodiment

FIG. 7 (collectively 7A to 7E) shows a diagram illustrating one example fabrication process of the SERS sensing element 114 and 211 respectively of FIGS. 1 and 2 and the SERS substrates 312 and 512 respectively of FIGS. 3 and 5. As shown in FIGS. 7A to 7E, the sensing element and the SERS substrate (collectively structure 700) include nanostructures 702 fabricated by a nanoreplica process. These nanostructures include so-called "hot spots" that concentrate an incident electromagnetic field (e.g., laser light) and effectively amplify the localized near field. The SERS surface with periodic nanostructure 702 (e.g., nanodomes) is generated by nanoreplica molding process utilizing silicon masters fabricated by nanoimprint lithography (as shown in FIG. 7). The enhancement factor ("EF") of the SERS substrate using these nanostructures can achieve a value as high as $10^7$.

Figure 7A:
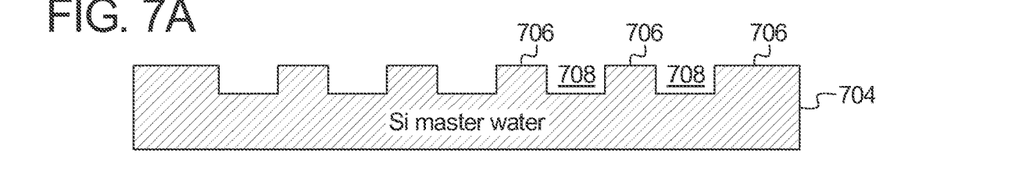
FIGS. 7A to 7E show diagrams illustrating a fabrication process of the sensing element of FIGS. 1 and 2 and the SERS substrates of FIGS. 3 and 5, according to an example embodiment of the present disclosure.
Figure 7B:
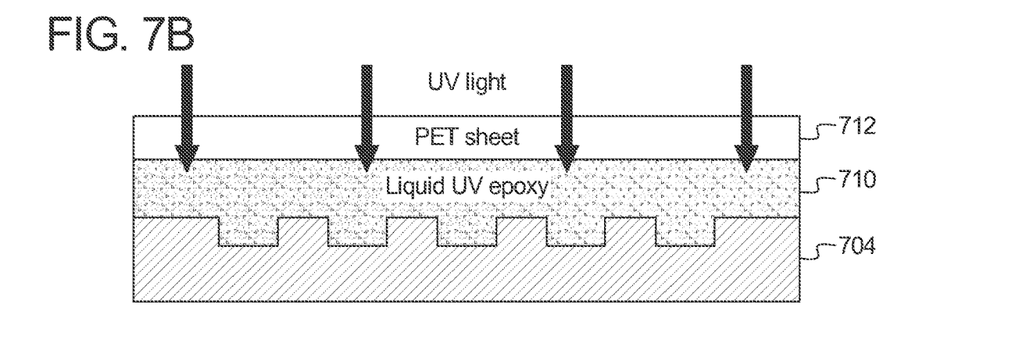
Figure 7C:
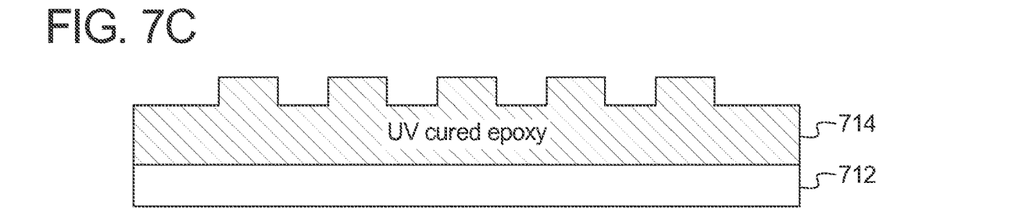
Figure 7D:
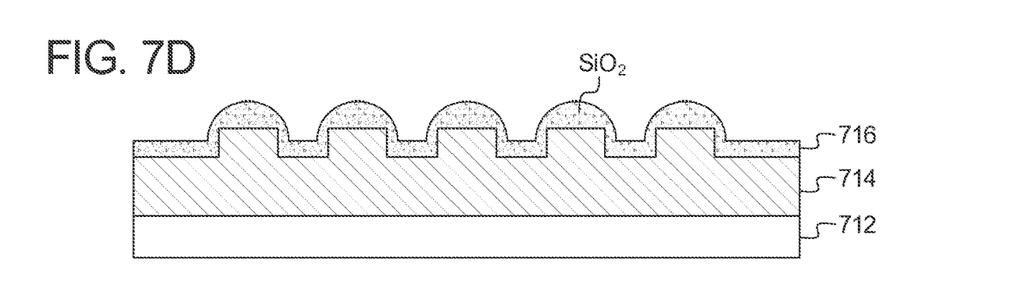
Figure 7E:
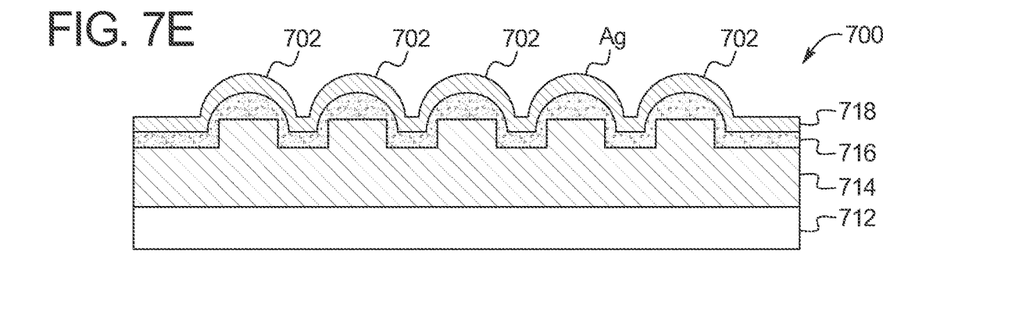

As shown in FIG. 7A, a silicon master wafer 704 is etched to include periodic lands 706 and valleys 708. In FIG. 7B, a liquid UV epoxy 710 and a PET sheet 712 is disposed on the master wafer 704. In FIG. 7C, the UV epoxy 710 and PET sheet 712 is cured using UV light to form a cured UV epoxy 714. In FIG. 7D, the master wafer 704 is removed and the remaining structure is flipped so that a front side of the UV epoxy 714 includes lands and valleys. In FIG. 7D, an insulating layer 716 of silicon dioxide $SiO_2$ is layered (e.g., deposited) on the UV epoxy 714 forming domes 702. In FIG. 7E, silver 718 is deposited on top of the silicon dioxide layer 716. It should be appreciated that silver may be replaced with any other type of conductive metal and/or substance for SERS sensing.

Figure 8:
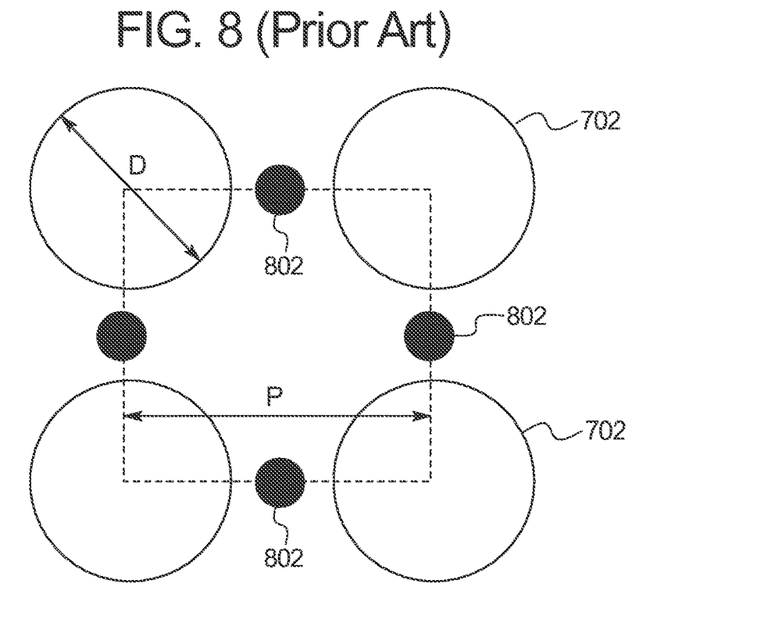
FIG. 8 shows a prior art nanopattern of nanostructures for the process discussed in connection with FIG. 7.

FIG. 8 shows a commonly used periodic nanopattern of the nanostructures disclosed in FIG. 7. In this example, the larger circles correspond to the nanodomes 702 of FIG. 7 and the smaller circles correspond to the hot spots 802. For any square defined by the centers of the nanodomes, the commonly used nanopattern includes two full hot spots.

Figure 9:
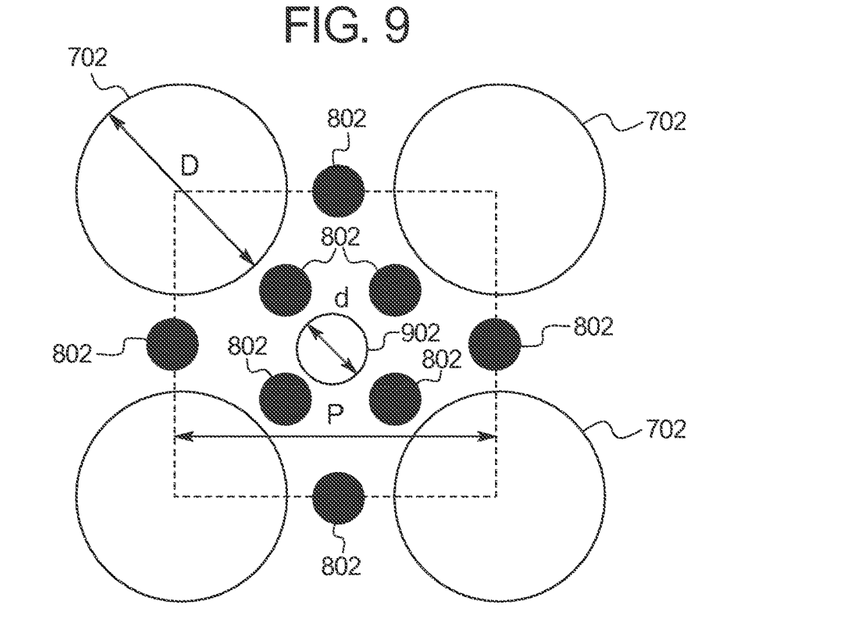
FIG. 9 shows a hybrid periodic nanostructure/pattern that increases a number of hot spots to improve an enhancement factor of the sensing element of FIGS. 1 and 2 and the SERS substrates of FIGS. 3 and 5, according to an example embodiment of the present disclosure.

FIG. 9 shows a hybrid periodic nanostructure/pattern according to the present disclosure that increases the number of hot spots to improve the enhancement factor of the SERS substrate and/or sensing elements. In this embodiment, a smaller sized nanostructure or nanodome 902 is placed within a center of the four larger nanodomes 702. In order to maintain the distance between adjacent nanostructures, equation (1) is used:

$$d=\sqrt{2}P-D-2(P-D)=D-(2-\sqrt{2})P \qquad (1)$$

In equation (1) d is the diameter of the smaller sized nanostructure 902. P is the distance between the centers of the larger nanodomes 702 and D is a diameter of the larger nanodomes 702. In an example where D is equal to 300 nanometers, P is equal to 400 nanometers, d is determined to be 66 nanometers. As a result of this configuration, the number of hot spots 802 within the dotted square has been tripled from two (in the case of the prior art example) to six for the same covered area. This configuration accordingly improves the signal or accuracy of the SERS substrates and sensing elements.

Additional Aspects of the Present Disclosure

To the above ends, and without limiting the following description, in a first aspect of the present disclosure, a disposable set includes a tube and a sensing member insertable into the tube, the sensing member including a first end having a first diameter and including at least one through hole positioned along a perimeter of the first end, a second end having a second diameter and including at least one through hole positioned along a perimeter of the second end, the second diameter being substantially equal to the first diameter, and a middle portion located between the first end and the second end having a diameter that is less than the first diameter, the middle portion including at least one surface enhanced Raman spectroscopy ("SERS") sensing element.

In accordance with a second aspect of the present disclosure, which may be used in combination with the first aspect, the SERS sensing element includes nanostructures disposed upon a plastic sheet.

In accordance with a third aspect of the present disclosure, which may be used in combination with any one or more of the preceding aspects, the tube includes a first interior wing configured to fix the first end of the sensing member in place within the tube.

In accordance with a fourth aspect of the present disclosure, which may be used in combination with any one or more of the preceding aspects, the tube includes a second interior wing configured to fix the second end of the sensing member in place within the tube.

In accordance with a fifth aspect of the present disclosure, which may be used in combination with any one or more of the preceding aspects, the tube includes at least one exterior wing configured to align a sensing device with the sensing member.

In accordance with a sixth aspect of the present disclosure, which may be used in combination with any one or more of the preceding aspects, the first end and the second end each include at least six through holes positioned circumferentially along the respective perimeter.

In accordance with a seventh aspect of the present disclosure, which may be used in combination with any one or more of the preceding aspects, a disposable set includes a tube and a sensing member insertable into the tube, the sensing member including a first end including a first plurality of spokes that extend from the first end to a first outer ring having a first diameter, a second end including a second plurality of spokes that extend from the second end to a second outer ring having a second diameter, the second diameter being substantially equal to the first diameter, and a middle portion located between the first end and the second end having a diameter that is less than the first diameter, the middle portion including at least one SERS sensing element.

In accordance with a eighth aspect of the present disclosure, which may be used in combination with any one or more of the preceding aspects, the spokes of the first end and the second end are compressible to enable the sensing member to be press-fitted into the tube.

In accordance with a ninth aspect of the present disclosure, which may be used in combination with any one or more of the preceding aspects, the disposable set includes a first set of spaces defined between the first end, the first plurality of spokes, and the first outer ring configured to enable fluid to flow through and a second set of spaces defined between the second end, the second plurality of spokes, and the second outer ring configured to enable the fluid to flow through.

In accordance with a tenth aspect of the present disclosure, which may be used in combination with any one or more of the preceding aspects, the tube includes a circular interior wing configured to fix the first outer ring of the sensing member in place within the tube.

In accordance with a eleventh aspect of the present disclosure, which may be used in combination with any one or more of the preceding aspects, the SERS sensing element includes nanostructures arranged within a grid pattern.

In accordance with a twelfth aspect of the present disclosure, which may be used in combination with any one or more of the preceding aspects, the nanostructures include a smaller sized nanostructure located within a center of four larger nanostructures.

In accordance with a thirteenth aspect of the present disclosure, which may be used in combination with any one or more of the preceding aspects, the smaller sized nanostructure has a diameter d according to the following equation $d=\sqrt{2}P-D-2(P-D)=D-(2-\sqrt{2})P$, wherein P is a distance between centers of the larger nanostructures and D is a diameter of the larger nanostructures.

In accordance with a fourteenth aspect of the present disclosure, which may be used in combination with any one or more of the preceding aspects, a disposable set includes a tube including an opening positioned along a portion of a wall of the tube and an enclosure connected to the tube at the opening, the enclosure including (i) a first end including a SERS substrate positioned to be substantially flush with an interior wall of the tube at the opening, (ii) at least one post to support the SERS substrate at the opening, (iii) a second end configured to align a sensing device with the SERS substrate, and (iv) a channel located between the first end and the second end configured to enable light from the sensing device to reach the SERS substrate.

In accordance with a fifteenth aspect of the present disclosure, which may be used in combination with any one or more of the preceding aspects, the channel includes a lens configured to focus the light from the sensing device on the SERS substrate.

In accordance with a sixteenth aspect of the present disclosure, which may be used in combination with any one or more of the preceding aspects, the second end includes an alignment key configured to align a corresponding lens of the sensing device with the SERS substrate.

In accordance with a seventeenth aspect of the present disclosure, which may be used in combination with any one or more of the preceding aspects, the tube includes a second opening positioned along a second portion of the wall of the tube.

In accordance with a eighteenth aspect of the present disclosure, which may be used in combination with any one or more of the preceding aspects, the disposable set further includes a second enclosure connected to the tube at the second opening, the second enclosure including (a) a first end including a window positioned to be substantially flush with the interior wall of the tube at the second opening, (b) a second end configured to align a second sensing device with the window, and (c) a channel located between the first end and the second end configured to enable light from the second sensing device to reach the window.

In accordance with a nineteenth aspect of the present disclosure, which may be used in combination with any one or more of the preceding aspects, the sensing device includes a SERS analyzer and the second sensing device includes a Raman spectroscopy analyzer.

In accordance with a twentieth aspect of the present disclosure, which may be used in combination with any one or more of the preceding aspects, the second opening is located between 1 centimeter and 24 centimeters from the opening.

In accordance with a twenty-first aspect of the present disclosure, any of the structure and functionality illustrated and described in connection with FIGS. 1 to 9 may be used in combination with any of the structure and functionality illustrated and described in connection with any of the other of FIGS. 1 to 9 and with any one or more of the preceding aspects.

Conclusion

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

For example the disposable set of FIGS. 1 to 6 was described as being part of an IV system and could include a catheter, a connection to an infusion bag, a connection to an infusion pump, etc. It should be appreciated that the disclosed disposable set could also be included within a drug compounding system to measure fluid type and/or concentration prior to entering a compounding device and/or after exiting a compounding device. Moreover, the disposable set could be used in renal applications including, for example, hemofiltration, hemodialysis, etc.

The invention is claimed as follows:

1. A disposable set including:
 a tube; and
 a sensing member located inside the tube, the sensing member including:
  a first end having a first diameter and including at least one through hole positioned along a perimeter of the first end;
  a second end, parallel to the first end, having a second diameter and including at least one through hole positioned along a perimeter of the second end, the first diameter and the second diameter being substantially equal to a diameter of an inner wall of the tube to form a seal between the first and second ends and the inner wall of the tube; and
  a middle portion located between the first end and the second end having a diameter that is less than the first diameter, the middle portion including at least one surface enhanced Raman spectroscopy ("SERS") sensing element that is located on an exterior surface of the middle portion, wherein the at least one through hole in the first end and the at least one through hole in the second end are configured to enable fluid to pass over the sensing member.

2. The disposable set of claim 1, wherein the tube includes at least one of:
 a first interior wing configured to fix the first end of the sensing member in place within the tube;
 a second interior wing configured to fix the second end of the sensing member in place within the tube; or
 at least one exterior wing configured to align a sensing device with the sensing member.

3. The disposable set of claim 1, wherein the first end and the second end each include at least six through holes positioned circumferentially along the respective perimeter.

4. The disposable set of claim 1, wherein the sensing member is press-fittingly insertable into the tube.

5. The disposable set of claim 1, wherein the tube is formed around the sensing member.

6. A disposable set including:
 a tube; and
 a sensing member located inside the tube, the sensing member including:
  a first end including a first plurality of spokes that extend from the first end to a first outer ring having a first diameter;
  first spaces defined between the first end, the first plurality of spokes, and the first outer ring;
  a second end, parallel to the first end, including a second plurality of spokes that extend from the second end to a second outer ring having a second diameter, the second diameter being substantially equal to the first diameter;
  second spaces defined between the second end, the second plurality of spokes, and the second outer ring; and
  a middle portion located between the first end and the second end having a diameter that is less than the first diameter, the middle portion including at least one surface enhanced Raman spectroscopy ("SERS") sensing element that is located on an exterior surface of the middle portion, wherein the first spaces and the second spaces are configured to enable fluid to pass over the sensing member,
 wherein the first diameter and the second diameter are substantially equal to a diameter of an inner wall of the tube to form a seal between the first and second ends and the inner wall of the tube.

7. The disposable set of claim 6, wherein the spokes of the first end and the second end are compressible to enable the sensing member to be press-fitted into the tube.

8. The disposable set of claim 6, further comprising:
 a first set of spaces defined between the first end, the first plurality of spokes, and the first outer ring configured to enable fluid to flow through; and
 a second set of spaces defined between the second end, the second plurality of spokes, and the second outer ring configured to enable the fluid to flow through.

9. The disposable set of claim 6, wherein the SERS sensing element includes nanostructures arranged within a grid pattern, the nanostructures including a smaller sized nanostructure located within a center of four larger nanostructures.

10. The disposable set of claim 9, wherein the smaller sized nanostructure has a diameter d according to the following equation:

$$d = \sqrt{2}P - D - 2(P-D) = D - (2-\sqrt{2})P$$

wherein P is a distance between centers of the larger nanostructures and D is a diameter of the larger nanostructures.

11. The disposable set of claim 6, wherein the sensing member is press fittingly insertable into the tube.

12. The disposable set of claim 6, wherein the tube is formed around the sensing member.

13. A sensing apparatus including:
 a first end having a first diameter and including at least one through hole positioned along a perimeter of the first end;
 a second end, parallel to the first end, having a second diameter and including at least one through hole positioned along a perimeter of the second end; and
 a middle portion located between the first end and the second end having a diameter that is less than the first diameter, the middle portion including at least one surface enhanced Raman spectroscopy ("SERS") sensing element that is located on an exterior surface of the middle portion,
 wherein the at least one through hole in the first end and the at least one through hole in the second end enable fluid to pass over the sensing member.

14. The sensing apparatus of claim 13, wherein the first end and the second end each include at least six through holes positioned circumferentially along the respective perimeter.

15. The sensing apparatus of claim 13, wherein the SERS sensing element includes nanostructures arranged within a grid pattern, the nanostructures including a smaller sized nanostructure located within a center of four larger nanostructures.

16. The sensing apparatus of claim 15 wherein the smaller sized nanostructure has a diameter d according to the following equation:

$$d = \sqrt{2}P - D - 2(P-D) = D - (2-\sqrt{2})P \qquad (5)$$

wherein P is a distance between centers of the larger nanostructures and D is a diameter of the larger nanostructures.

* * * * *